(12) United States Patent
Azar

(10) Patent No.: US 6,660,009 B1
(45) Date of Patent: Dec. 9, 2003

(54) FRACTURE FIXATION SYSTEM

(76) Inventor: Carlos A. Azar, 355 Casaurina Concourse, Coral Gables, FL (US) 33143

( * ) Notice: Subject to any disclaimer, the term of this patent is extended or adjusted under 35 U.S.C. 154(b) by 37 days.

(21) Appl. No.: 10/144,707

(22) Filed: May 15, 2002

(51) Int. Cl.[7] .............................................. A61B 17/56
(52) U.S. Cl. ...................................................... 606/72
(58) Field of Search ............................ 606/60, 67, 72, 606/104, 75, 64; 411/439

(56) References Cited

U.S. PATENT DOCUMENTS

| | | | |
|---|---|---|---|
| 3,763,855 A | | 10/1973 | McAtee |
| 4,011,863 A | * | 3/1977 | Zickel ........................... 606/73 |
| 4,055,172 A | | 10/1977 | Ender et al. |
| 4,135,506 A | * | 1/1979 | Ulrich ........................... 606/61 |
| 4,667,663 A | | 5/1987 | Miyata |
| 4,712,541 A | * | 12/1987 | Harder et al. .................. 606/67 |
| 5,013,314 A | * | 5/1991 | Firica et al. ................... 606/64 |
| 5,135,527 A | * | 8/1992 | Ender ............................ 606/62 |
| 5,281,225 A | * | 1/1994 | Vicenzi ......................... 606/62 |
| 6,019,762 A | * | 2/2000 | Cole ............................. 606/72 |
| 6,074,392 A | | 6/2000 | Durham |
| 6,231,576 B1 | | 5/2001 | Frigg et al. |
| 6,273,892 B1 | | 8/2001 | Orbay et al. |
| 2003/0149433 A1 | * | 8/2003 | Hehli et al. ................... 606/69 |

* cited by examiner

*Primary Examiner*—Eduardo C. Robert
(74) *Attorney, Agent, or Firm*—Richard C. Litman (57) ABSTRACT

A nail fixation system and method for the fixation of fractures of the distal radius. The system has a nail inserter and a plurality of arcuate nails, each nail having a head end and a pointed end. Each nail is secured by its head end in the nail inserter and fed through one of several holes cut into the distal radius proximal to the fracture. The curvature of each nail and the angulation of each hole allows each nail to travel through the medullary canal of the radius and then have its point be positioned in a specific site internally on the distal epiphysis. Once the distal radius is fixed the entire wrist is placed in a cast for several weeks until the radius is healed sufficiently for the removal of the nails.

11 Claims, 7 Drawing Sheets

FRACTURE FIXATION SYSTEM

BACKGROUND OF THE INVENTION

1. Field of the Invention

The present invention relates to surgical tools and a method of use thereof, and more particularly, to arcuate surgical nails and a method of using said nails to fixate a fracture of the distal radius.

2. Description of the Related Art

The distal radius joint is an inherently unstable joint due to its osseous geometry. Due to this instability, fractures of the distal radius must often be fixed in position after reduction to insure proper healing. While the related art is replete with a variety of bone fixation devices none are specifically designed for the fixation of the distal radius with a minimum of tissue disturbance and a minimum of periosteal involvement.

For example, U.S. Pat. No. 3,763,855 to McAtee discloses a medical device for the fixation of the ulna, in particular fixing the enlarged end of the ulna, the olecranon, against the forces generated by the strong pull of the triceps muscle. The device itself is a long rod which is inserted into the medullary canal of the ulna. The '855 patent differs from the present invention in that it consists of only one long nearly straight nail, rather than a group of smaller arcuate nails.

U.S. Pat. No. 4,055,172 to Ender et al., U.S. Pat. No. 4,667,663 to Miyata and U.S. Pat. No. 6,231,576 to Frigg et al., disclose long intra-medullary nails for correctly resetting fractured long bones such as the femur, for their immediate reuse. These patents teach inserting long flexible nails into one end of a long bone, and then through the medullary canal and into the fracture area. The fracture is then reduced by rotating the nail. The nail also functions to fix the fracture. The inventions described above differ from the present invention in that the present invention uses several shorter nails that are not capable of traveling from one end of a long bone to the other. Each nail is uniquely arcuate to be positioned in a specific position in the distal radius with a minimum of tissue disturbance.

U.S. Pat. No. 6,074,392 to Durham discloses a method and device for use in bone fixation procedures. The invention consists of a curved guide and associated pin. The guide is used to locate the pin at the desired entry point on the bone and the pin is tapped or hammered into place. The pin is then used as a guide for a reamer which clears space for an inter-medullary rod. The '392 invention differs from the present invention in that the present invention uses multiple arcuate nails that cooperate to fix a fracture of the distal radius. The arcuate nails used in the '392 invention function only to guide a reamer.

U.S. Pat. No. 6,273,892 to Orbay et al. discloses a fracture fixation system. The system is used for the insertion of a fixation pin into the medullary canal of a fractured metacarpal, metatarsal, or phalangeal bone for stable bone fixation. The system has one or more pins and an instrument for implanting the pins. The '892 invention is distinguishable from the present invention because the present invention has a number of arcuate pins specifically designed to fix the distal radius. The nails of the present invention are also sharp, as opposed to the blunt pins of the '892 invention.

None of the above inventions and patents, taken either singly or in combination, is seen to describe the instant invention as claimed.

SUMMARY OF THE INVENTION

The present invention is a set of surgical nails, a nail handler for inserting the nails into the radius, and a method of using the aforementioned tools to reduce and internally fix a fracture of the distal radius. Typically there are four nails used in the procedure. Each nail is made of stainless steel, is circular in cross section, has a headless first end and a pointed second end, and is 150 mm in length. Depending on the size of the radius to be reduced, the nails are either 1.5 mm or 2 mm in thickness. The shank of each nail is arcuate adjacent the pointed end, with the amount of curvature varying from nail to nail.

The nail handler has a body and a compression nut. The body is cylindrical in shape with two opposing ends. A hole capable of receiving a nail is defined in one end of the body. The portion of the body surrounding the hole (nail receiving end) is cut into four flexible sections and is externally threaded. The balance of the external surface of the body is knurled to enhance grip. The compression nut is internally threaded so as to be rotatably attachable to the threaded nail receiving end of the body.

The aforementioned instruments are used in conjunction with a novel method of fixing fractures of the distal radius. The method involves first making an incision proximally along the radial styloid of the distal radius and dissecting the soft tissues therein. The fracture is approached between the compartment of the abductor pollicis longus and the extensor carpi radialis brevis. From there the fracture is approached from the radial, and if needed, the dorsal aspect of the radius.

The fracture itself is reduced using traction, counter traction and rotation, all performed under imaging intensified x-ray control. Once reduced, the fracture is ready for internally fixation. Four holes are drilled in the radial aspect of the radius. The holes are aligned so one of the nails may be positioned in each hole such that the nails travel through the medullary canal and into the subcortical area of the distal radius.

Accordingly, it is a principal object of the invention to provide a set of nails and a nail insertion tool capable of fixing a fracture of the distal radius.

It is another object of the invention to provide a surgical method of distal radius reduction and fixation which creates a minimum of disturbance to the associated tissues and bone.

It is a further object of the invention to provide a surgical method and fixation kit that obviates the risk of tendon ruptures and reactions and does not compromise the vascularity of the distal radius.

Still another object of the invention is to provide a fracture fixation system and method of using the system for fixation of a fracture of the distal radius that is easy to preform, teach and learn.

It is an object of the invention to provide improved elements and arrangements thereof in an apparatus for the purposes described which is dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
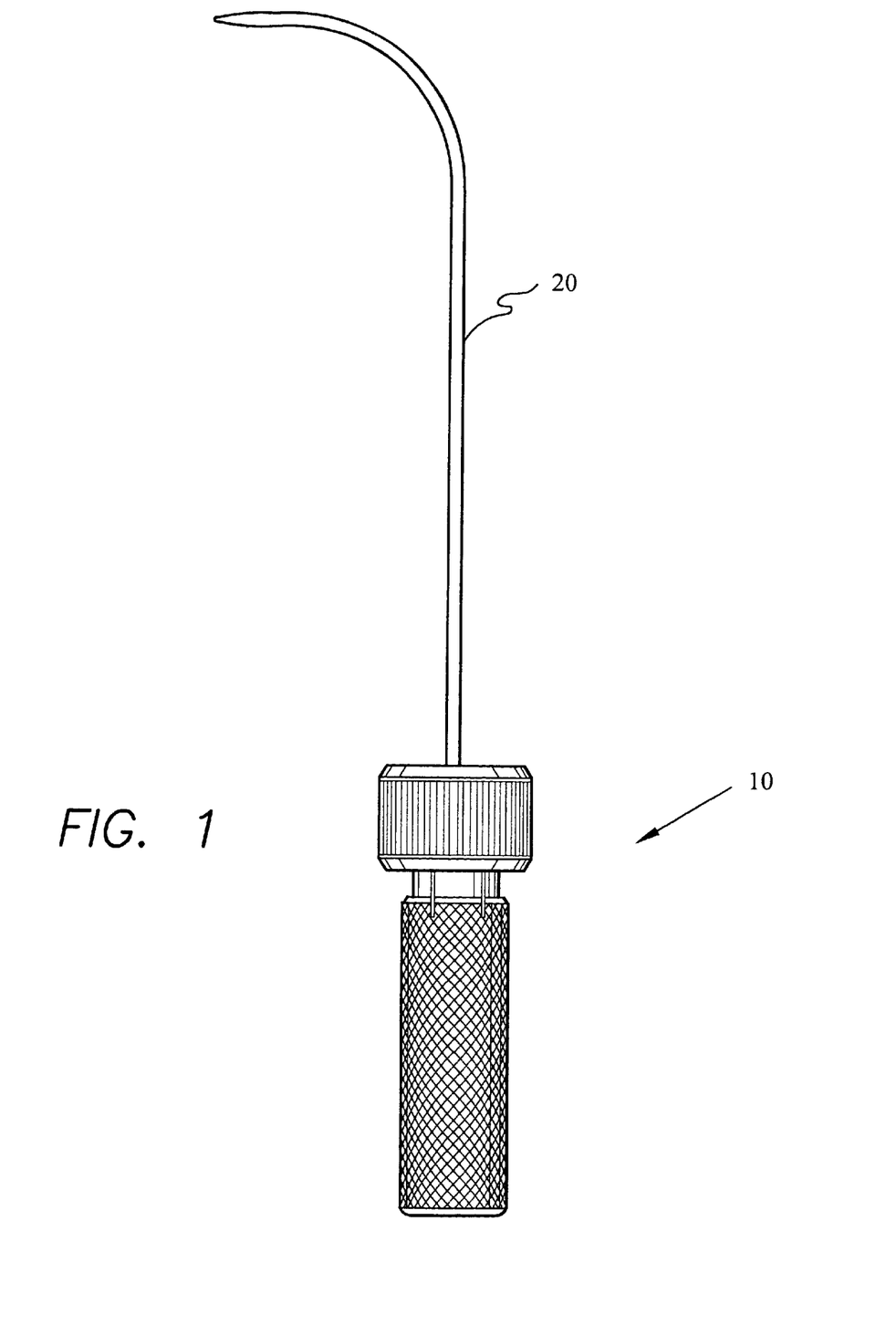
FIG. 1 is an elevation view of a nail and insertion tool of a fracture fixation system according to the present invention.

The present invention is a fracture fixation system for fixation of the reduced fragments of a distal radius fracture. As shown in FIG. 1, the invention includes a nail insertion tool 10 which is used to insert an arcuate nail 20 into a distal radius. Several arcuate nails 20, 30, 40, 50, shown in FIGS. 2A–2D, each having a distinct, predetermined curvature, are required for the procedure. Each arcuate nail 20, 30, 40, 50 is preferably formed from a straight 150 mm stainless steel nail 60 (FIG. 2E) having a sharp point at a second end 62 and a headless first end 64, the nail being bent to the required degree of curvature. The headless first end 64 of the nail 60 is formed by a straight crosscut orthogonal to an axis through the shank of the nail 60. The thickness of the nails 20–60 may vary between 1.5 and 2 mm depending on the size of the fractured bone to be fixed. Nail strength is approximately 410 Brinell (41 Rockwell).

Figures 2A, 2B, 2C:
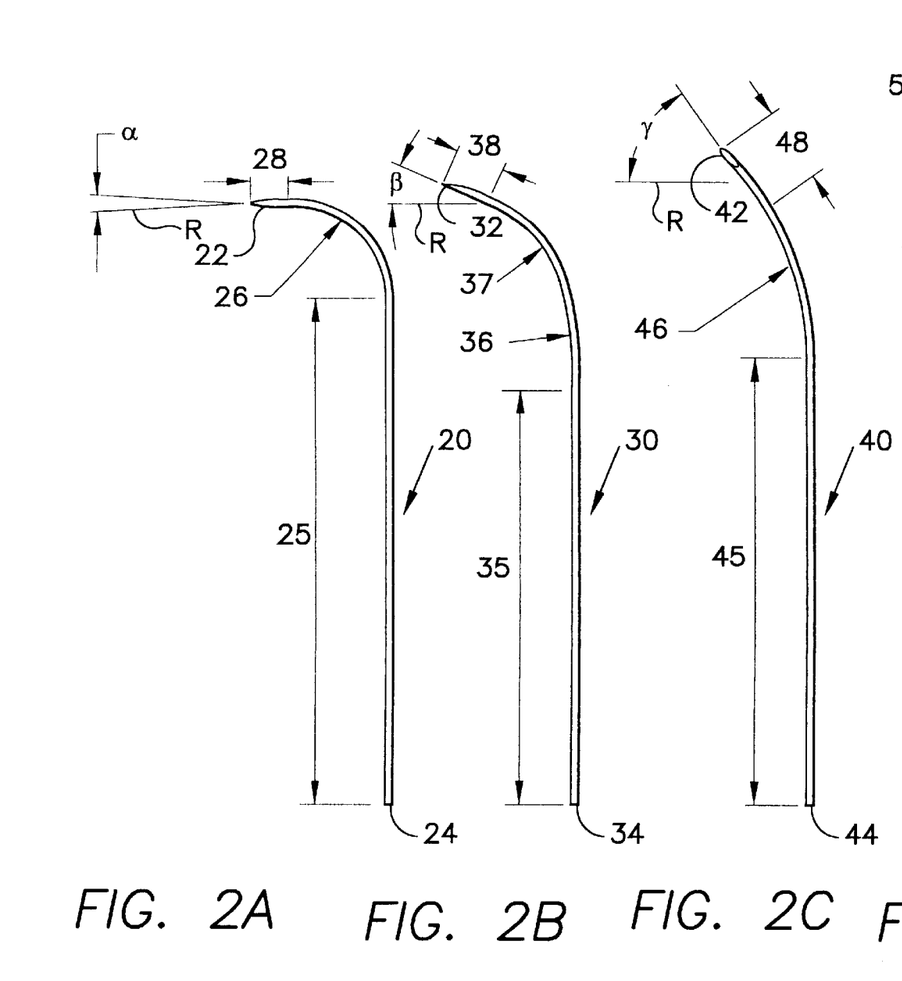
FIG. 2A is an elevation view of a first fixation nail according to the present invention.
FIG. 2B is an elevation view of a second fixation nail according to the present invention.
FIG. 2C is an elevation view of a third fixation nail according to the present invention.

FIG. 2A illustrates a first nail 20 used in the fracture fixation system. The nail has a sharp point 22 with 3 to 4 faces. From the headless first end 24 the nail has a straight section 25 extending for approximately 110 mm. Reference line R is perpendicular to straight shank section 25. Shank section 25 is tangent to arcuate nail section 26. Arcuate section 26 has a radius of curvature of 20.4 mm and a length of 33 mm. End section 28 of the nail is straight, 7 mm in length and is also tangent to the arcuate section 26. End section 28 ends at pointed second end 22. Angle α preferably measures about one degree.

FIG. 2B illustrates a second nail 30 used in the fracture fixation system. The nail 30 has a sharp point 32 with 3 or four faces and a headless first end 34. From the headless end 34 the nail has a straight shank section 35 extending for approximately 91 mm. Reference line R is perpendicular to shank section 35. Section 35 is tangent to a first arcuate nail section 36. Section 36 has a radius of curvature of 88 mm and is followed by a second arcuate section 37 with a radius of curvature of 31.5 mm. The combined length of arcuate sections 36 and 37 is about 49.5 mm. Arcuate section 37 is tangent to straight end section 38. Section 38 is 9.5 mm in length and leads to pointed second end 32. Angle β is preferably about 23 degrees.

FIG. 2C illustrates a third nail 40 used in the fracture fixation system. The nail 40 has a sharp point 42 with 3 or four faces and a headless first end 44. From the headless end 44 the nail has a straight shank section 45 extending for approximately 98 mm. Reference line R is perpendicular to shank section 45. Section 45 is tangent to arcuate nail section 46. Arcuate section 46 has a radius of curvature of 56 mm and a length of 35.5 mm. End section 48 of the nail is straight, 16.5 mm in length and is also tangent to the arcuate section 46. Section 48 ends at point 42. Angle γ is preferably 56 degrees.

Figure 2D:
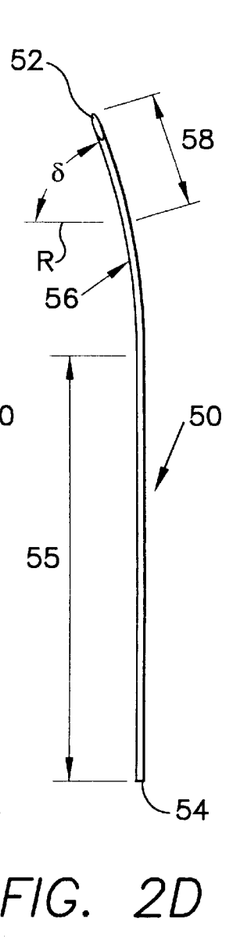
FIG. 2D is an elevation view of a fourth fixation nail according to the present invention.
Figure 2E:
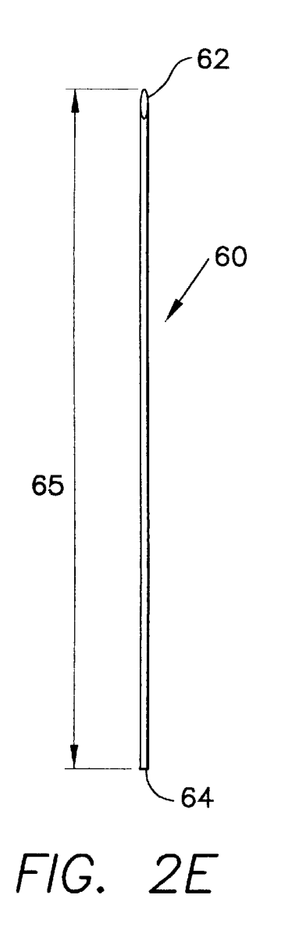
FIG. 2E is an elevation view of a straight nail for reference purposes.

FIG. 2D illustrates a fourth nail 50 used in the fracture fixation system. The nail 50 has a sharp point 52 with 3 or four faces and a headless first end 54. From the headless end 54 the nail has a straight shank section 55 extending for approximately 94 mm. Reference line R is perpendicular to shank section 55. Section 55 is tangent to arcuate nail section 56. Arcuate section 56 has a radius of curvature of 92 mm and a length of 30 mm. End section 58 of the nail is straight, 26 mm in length and is also tangent to the arcuate section 56. Section 58 ends at point 52. Angle δ is preferably about 72 degrees.

Figure 3:
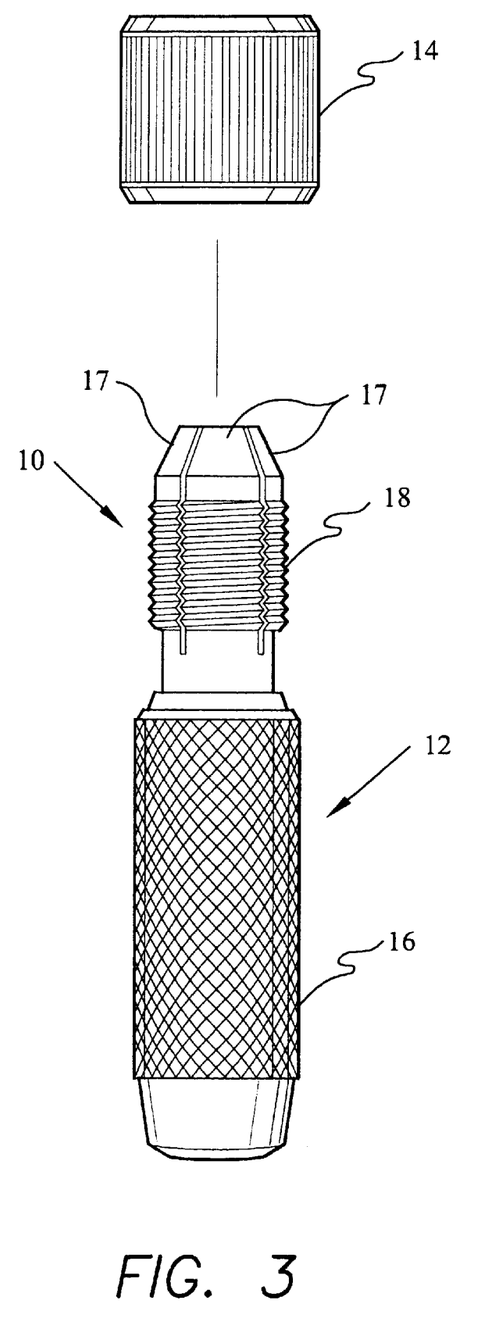
FIG. 3 is a partially exploded view of the nail inserter and compression nut.
Figure 4:
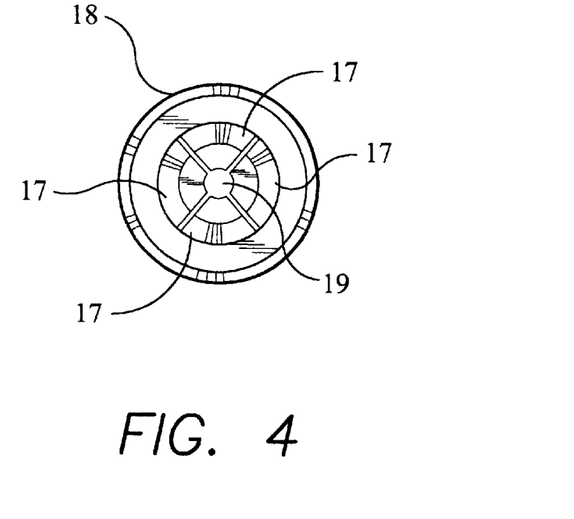
FIG. 4 is a top view of the nail inserter and compression nut.

FIG. 3 illustrates an exploded view of the nail insertion tool 10. The nail inserter 10 has a cylindrical body with a knurled handle portion 16, a nail holder portion 18 and a circular compression nut 14. The nail inserter 10 may be made from a temperature-resistant durable material such as aluminum, nylon 6 or stainless steel. The nail holder portion 18, as shown in FIG. 4, is cut into four sections 17 which define a central hole 19. When in use a nail is captured with the headless first end inserted into the hole 19. The compression nut 14 is then screwed onto the nail holder 18, which compresses the four sections 17 of the nail holder 18 towards the center of the hole 19. The compressive forces will thereby secure the nail in the nail inserter 10.

Figure 5:
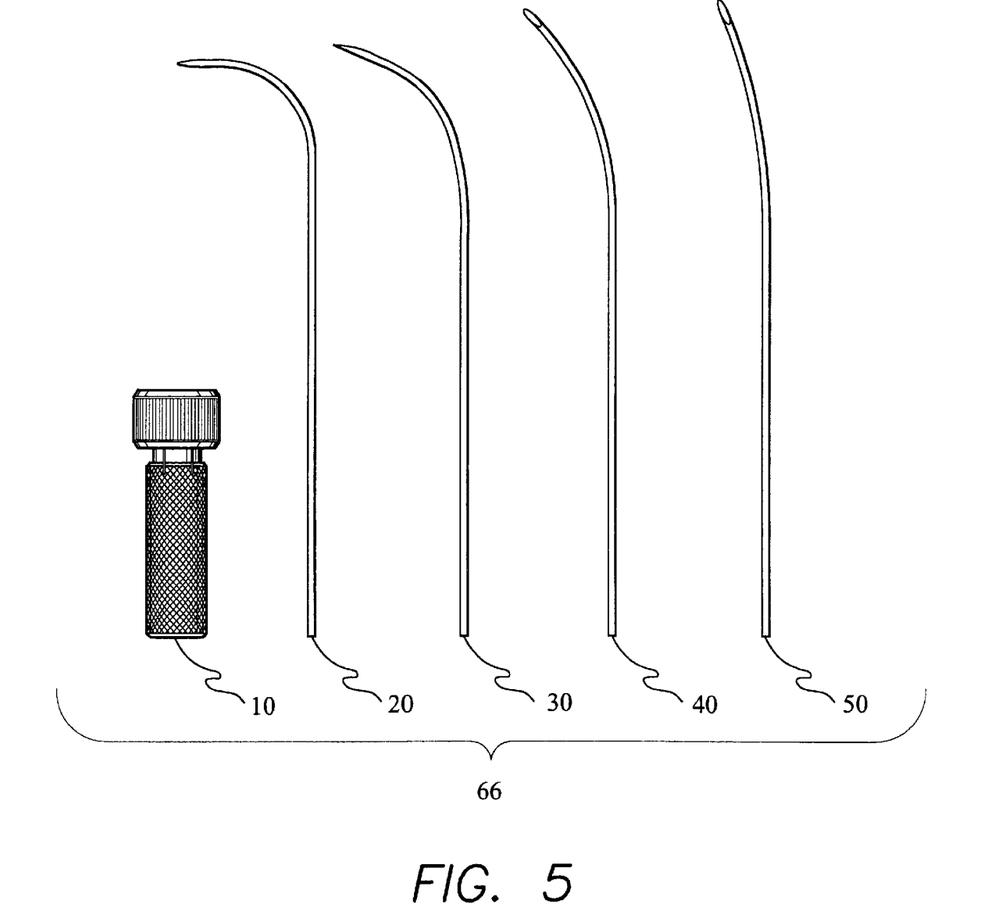
FIG. 5 is an elevation view of a fracture fixation kit according to the present invention.

Nails 20, 30, 40, 50, combined with the nail inserter 10, form a surgical kit 66 as illustrated in FIG. 5. The kit is used in conjunction with a novel surgical method (discussed below) to reduce and fix displaced fractures of the distal radius.

The first step in the surgical method is making an incision in the soft tissues above the radial aspect of the distal radius from the radial styloid proximally for a length of approximately 5 cm. The soft tissues are then dissected and the distal radius styloid and fracture are approached between the compartment of the abductor pollicis longus and the extensor carpi radialis brevis. Then the dissection is carried more proximally, the abductor pollicis longus is retracted dorsally towards the ulna and then the dissection is continued between the abductor pollicis longus and the brachial radialis tendon. The sensory branches of the radial nerve are retracted and the fracture of the distal radius is approached through the radial, and if necessary the dorsal aspect. The fracture is then reduced under imaging intensified x-ray control using traction, counter traction and rotation.

If any difficulty is encountered reducing the fracture due to the deforming processes of the brachio radial tendon, the tendon is easily accessed and released from the above mentioned incision location. The approach also allows for easy access to the fracture itself for the elevation of any impacted fracture or the release of a fracture callous. Once any fracture complications are taken care of and the imaging intensifier x-ray shows the proper alignment of the fracture, the fracture is ready for internal fixation.

Some fractures of the distal radius, unlike the above mentioned situation, can be reduced externally and have no deforming forces that need to be released. These situations require a substantially smaller surgical approach. The incision is started just proximally from the fracture line and extends proximally for about 3.5 cm. Then the dissection is carried out between the brachial radialis tendon and the abductor pollicis longus tendon. The distal radius bone is then approached. This approach causes a minimum of disturbance to the fracture hematoma. The following steps of nail insertion are the same for both of the aforementioned fracture situations (deforming and non-deforming).

The first step of internal fixation is the drilling of one of several holes into the medullary canal of the distal radius. Each hole should be large enough to accommodate one of the aforementioned arcuate nails and be drilled at an inclination which accounts for the curvature and the final position of the chosen nail. The nail insertion process is ordinarily done under image intensifier x-ray control following the curve of the nail. The nail can inserted by hand or can be kindly tapped or hammered into position.

Figure 6:
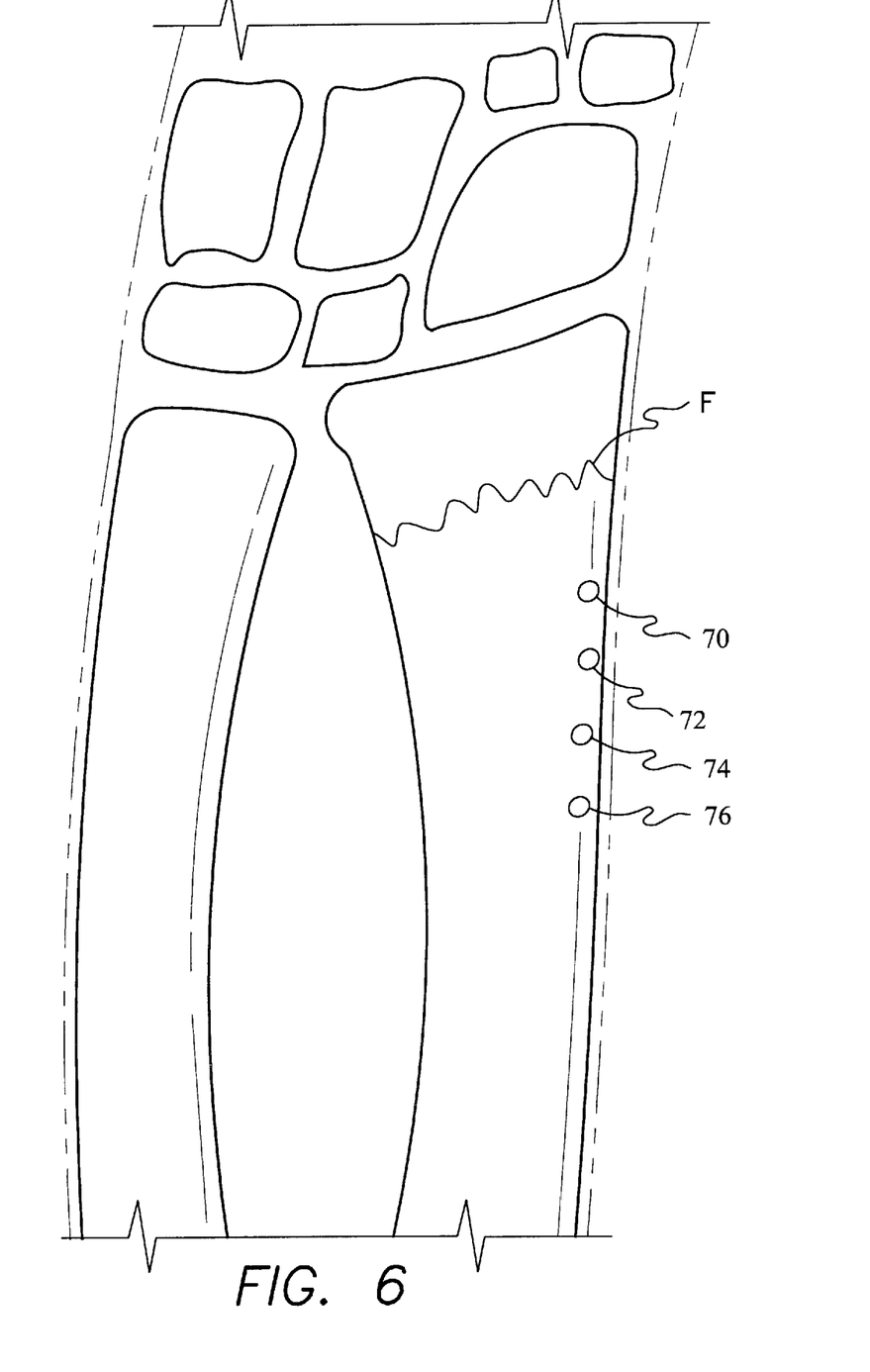
FIG. 6 is a diagrammatic view of an ulna and radius, showing exemplary locations for drilled nail insertion holes.

FIG. 6 illustrates the approximate positions of the aforementioned holes. The first hole 70 should be positioned on the radial aspect of the radius bone approximately 2 cm proximal to the fracture line F. Nail 20 is then inserted into the hole 70 with the assistance of the nail inserter 10. The hole 70 must be angled to allow the nail 20 to be fed through the medullary canal of the radius with the point 22 of the nail 20 being positioned in the subcortical area of the tip of the distal radial styloid process 80. Once the nail 20 is properly positioned, main control of the fracture is achieved. The nail inserter 10 is removed after a nail has been finally positioned.

A second drill hole 72 is then made on the radial aspect of the distal radius approximately 5 mm proximally to the first nail hole 70. The second nail 30 is then fed through the hole 72, using the nail inserter 10, until the nail point is placed in the subcortical area of the scaphoid facet of the distal radius.

A third hole 74 is then drilled approximately 5 mm proximally to hole 72 on the radial aspect of the distal radius. Then nail 40 is fed through the hole 74, using the nail inserter 10, until the point of the nail 40 is positioned into the subcortical area of the lunate facet of the distal radius.

Figure 7:
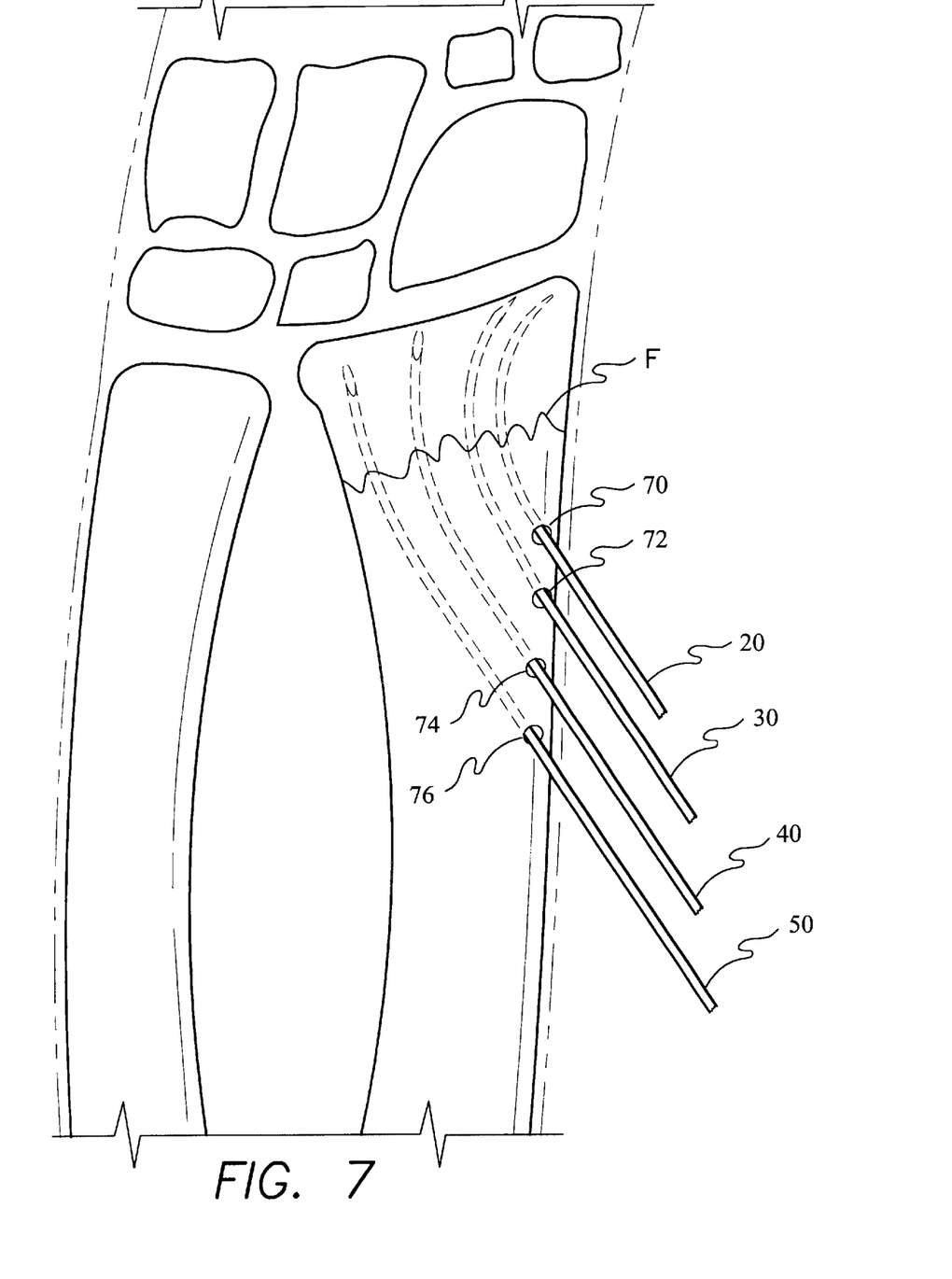
FIG. 7 is a diagrammatic view of the fixation nails inserted into the distal radius.

A fourth hole 76 is drilled about 5 mm proximally to nail hole 74 on the radial aspect of the distal radius. Then nail 50 is fed through the hole 76, using the nail inserter 10, until the point of the nail 50 is positioned in the subcortical area of the sigmoid notch of the distal radius. FIG. 7 shows the nails 20, 30, 40, 50 in the aforementioned positions in a patient's distal radius.

Figure 8:
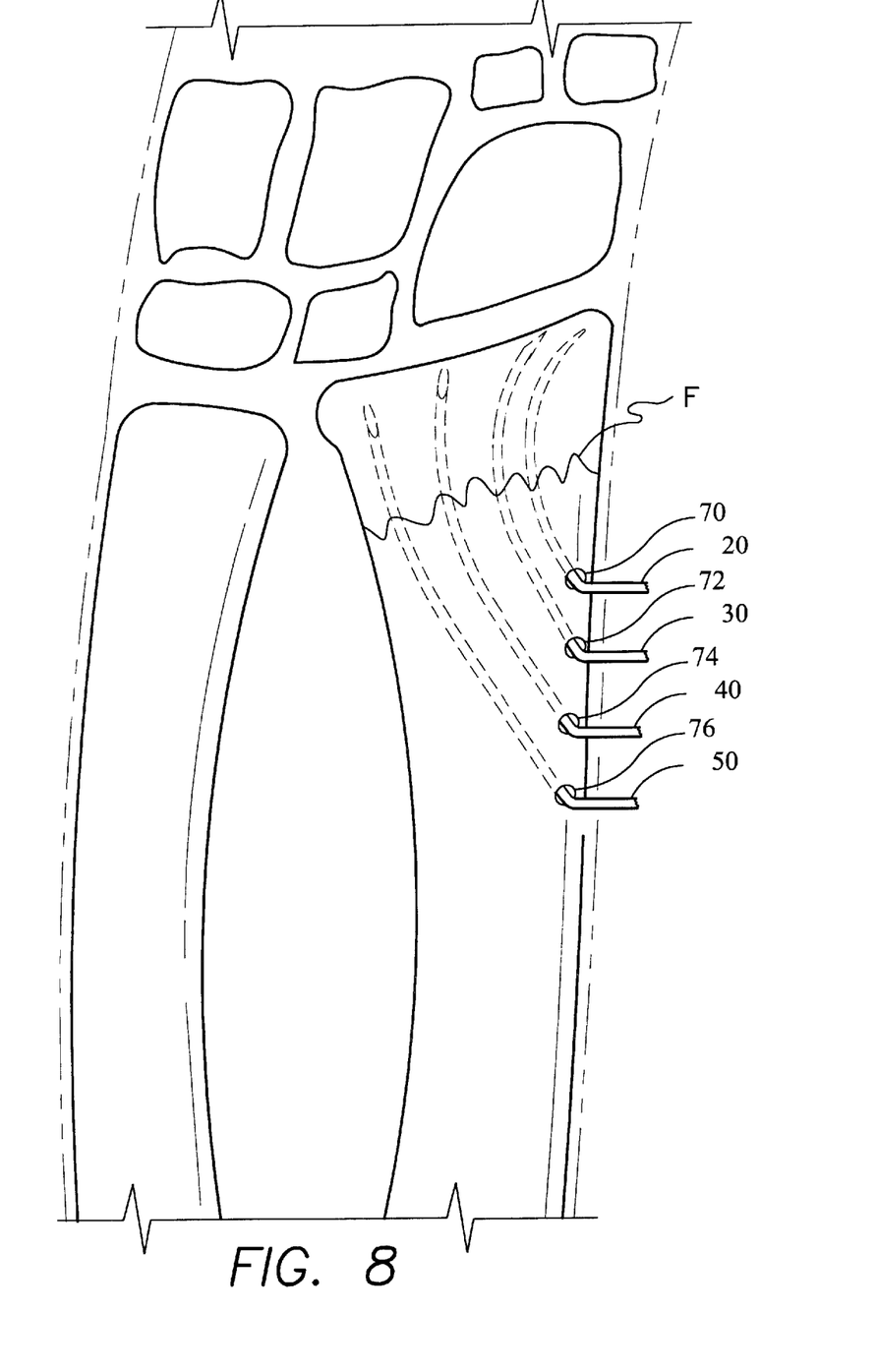
FIG. 8 is a diagrammatic view of the fixation nails inserted into the distal radius after bending of the nails.

Once the nails are in position the stability of the fracture is tested, under image intensifier x-ray control, by extension, flexion, pronation, supination, ulnar deviation and radial deviation. When a nail is introduced the nail may be rotated (dorsally for a dorsal die punch fracture, or volarly for a volar die punch fracture) to reach the specific fracture area. Pins may also be added if the fracture is not stable. In order to lock each nail into position, as shown in FIG. 8, each nail is bent to a 90 degree angle at each bone hole (70, 72, 74, 76). Each nail is then lightly tapped into position then cut leaving an approximately 1 cm length of nail extending from each hole.

The nails may be left in the subcutaneous tissue or can be left outside the epidermis with a proper protective device positioned on the end of the nails. The soft tissues are closed and the patient is put into a short arm volar splint immobilization device until the arm is ready for casting. After 4 to 6 weeks the cast is removed and after two additional weeks the nails are removed under local anesthetic.

It is to be understood that the present invention is not limited to the sole embodiment described above, but encompasses any and all embodiments within the scope of the following claims.

I claim:

1. A bone fixation system, comprising:

first, second, third, and fourth nails, each nail having a headless first end, a pointed second end, and a shank, the shank having an elongated straight section extending from the headless first end, a short straight end section terminating in the pointed second end, and an arcuate section therebetween, the arcuate section of the first, second, third and fourth nails each having a radius of curvature, the radius of curvature progressively increasing from the first nail to the fourth nail; and a nail inserter having a cylindrical body and a compression nut, the body having a nail insertion end and a grip end, and the compression nut being rotatably attachable to the grip end and thereby being capable of compressing said grip end in order to clamp the first end of said first, second, third and fourth nails.

2. A bone fixation system as in claim 1, wherein:

the elongated straight section of said first nail has a length of about 110 mm;

the arcuate section of said first nail has a radius of curvature of about 20.4 mm and a length of 33 mm; and the short straight end section of said first nail has a length of about 7 mm, the point having at least three faces.

3. A bone fixation system as in claim 1, wherein:

the elongated straight section of said second nail has a length of about 91 mm;

the arcuate section of said second nail has a first section with a radius of curvature of about 92 mm and a second section having a radius of curvature of about 31.5 mm, and a combined length of about 49.5 mm; and the short straight end section of said second nail has a length of about 9.5 mm, the point having at least three faces.

4. A bone fixation system as in claim 1, wherein:

the elongated straight section of said third nail has a length of about 98 mm;

the arcuate section of said third nail has a radius of curvature of about 56 mm and a length of about 35.5 mm; and the short straight end section of said third nail has a length of about 16.5 mm, the point having at least three faces.

5. A bone fixation system as in claim 1, wherein:

the elongated straight section of said fourth nail has a length of about 94 mm;

the arcuate section of said fourth nail has a radius of curvature of about 92 mm and a length of about 30 mm; and the short straight end section of said fourth nail has a length of about 26 mm, the point having at least three faces.

6. A bone fixation system as in claim 1, wherein said first, second, third and fourth nails are made of stainless steel.

7. A bone fixation system as in claim 1, wherein:

the nail insertion end of said body has four sections;

said compression nut has an inside and outside, with the outside having a friction inducing surface; and said grip end has a friction inducing surface.

8. A method of distal radius fracture fixation using the apparatus described in claim 1 comprising the following steps:

(a) creating an incision in the soft tissue above the distal radius, the incision running from the radial styloid proximally for a length of approximately 5 cm;

(b) dissecting the soft tissues in the area of said incision;

(c) reducing said fracture;

(d) drilling a first hole in the radial aspect of the radius bone about 2 cm proximal to the fracture line;

(e) inserting said first nail through said first hole into the medullary cavity of said distal radius with said point coming to rest in the subcortical area of the tip of the distal radial styloid process;

(f) drilling a second hole in the radial aspect of the radius bone, said second hole being positioned approximately 5 mm proximally to said first hole;

(g) inserting said second nail through said second hole into the medullary cavity of said distal radius with said point coming to rest in the subcortical area of the distal radial scaphoid facet;

(h) drilling a third hole in the radial aspect of the radius bone, said second hole being positioned approximately 5 mm proximally to said second hole;

(i) inserting said third nail through said third hole into the medullary cavity of said distal radius with said point coming to rest in the subcortical area of the lunate facet of the distal radius;

(j) drilling a fourth hole in the radial aspect of the radius bone, said second hole being positioned approximately 5 mm proximally to said third hole; and (k) inserting said fourth nail through said fourth hole into the medullary cavity of said distal radius with said point coming to rest in the subcortical area of the radial aspect of the sigmoid notch.

9. The method of distal radius fracture fixation as described in claim 8, including the following additional steps:

(l) bending each said nail to an approximately 90 degree angle at each said nail hole, lightly tapping each said nail into position, and cutting each said nail thereby leaving approximately 2 to 4 mm of said nail protruding from each said hole;

(m) returning the soft tissues to their proper positions and closing said incision;

(n) securing said distal radius and the associated forearm with a cast;

(o) removing said cast and said nails after the distal radius has healed.

10. The method as described in claim 8, wherein:

said fixation of said distal radius and the insertion said first, second, third and fourth nails into the distal radius is performed under image intensifier x-ray control.

11. The method as described in claim 8, wherein:

said reduction of said fracture requires releasing the brachio radial tendon.

* * * * *